United States Patent
Viaud-Massuard et al.

(10) Patent No.: US 9,427,719 B2
(45) Date of Patent: Aug. 30, 2016

(54) PROCESS FOR MANUFACTURING POLYSILOXANE MICROCAPSULES THAT ARE FUNCTIONALIZED AND ARE NOT VERY POROUS

(75) Inventors: Marie-Claude Viaud-Massuard, Tours (FR); Jeremy Monfray, Lyons (FR); Peggy Robert, Blois (FR); Elodie Raynaud, Mons (BE); Vincent Bouazza, Narbonne (FR)

(73) Assignee: UNIVERSITE DE TOURS FRANCOIS RABELAIS, Tours (FR)

( * ) Notice: Subject to any disclaimer, the term of this patent is extended or adjusted under 35 U.S.C. 154(b) by 0 days.

(21) Appl. No.: 13/823,328

(22) PCT Filed: Sep. 22, 2011

(86) PCT No.: PCT/FR2011/052192
§ 371 (c)(1),
(2), (4) Date: Mar. 14, 2013

(87) PCT Pub. No.: WO2012/038666
PCT Pub. Date: Mar. 29, 2012

(65) Prior Publication Data
US 2013/0181363 A1   Jul. 18, 2013

(30) Foreign Application Priority Data
Sep. 24, 2010  (FR) .................................... 10 57708

(51) Int. Cl.
*B01J 13/18* (2006.01)
*A61K 8/11* (2006.01)
(Continued)

(52) U.S. Cl.
CPC .................. *B01J 13/18* (2013.01); *A61K 8/11* (2013.01); *A61K 8/891* (2013.01); *A61K 8/898* (2013.01); *A61Q 19/00* (2013.01); *D06M 13/513* (2013.01); *D06M 23/12* (2013.01)

(58) Field of Classification Search
CPC ....................................................... B01J 13/18
See application file for complete search history.

(56) References Cited

U.S. PATENT DOCUMENTS 6,020,066 A * 2/2000 Weisser et al. .......... 428/402.21
6,855,335 B2 2/2005 Seok et al.
2011/0200654 A1 * 8/2011 Habar .......................... 424/401

FOREIGN PATENT DOCUMENTS

EP       0934773 A2    8/1999
EP       2080552       7/2009
WO    2010/045446 A2   4/2010

OTHER PUBLICATIONS

Japanese Office Action from Corresponding Japanese Patent Application No. 2013-529697, dated Apr. 21, 2015.

*Primary Examiner* — Jeffrey Washville
(74) *Attorney, Agent, or Firm* — Greer, Burns & Crain, Ltd.

(57) ABSTRACT

A method is provided for encapsulating products that can have lipophilic or hydrophilic, including volatile, properties in a polysiloxane membrane that is particularly impervious. A method is also provided for evaluating the imperviousness of capsules. The present method includes the following steps:
a) formation of droplets by an emulsion between an oily phase containing the product to be encapsulated and an acidic aqueous phase heated to around 50° C. and in the presence of surfactants;
b) addition and hydrolysis of at least one silane in order to obtain a silanol;
c) increasing the pH in order to start condensation of the silanol to form a first membrane around the droplets of the product to be encapsulated;
d) lowering the pH;
e) increasing the pH, optionally preceded by adding a silane, in order to obtain a new condensation of silanol around the droplets of the product to be encapsulated.

16 Claims, 1 Drawing Sheet

(51) Int. Cl.
*A61K 8/891* (2006.01)
*A61K 8/898* (2006.01)
*A61Q 19/00* (2006.01)
*D06M 13/513* (2006.01)
*D06M 23/12* (2006.01)

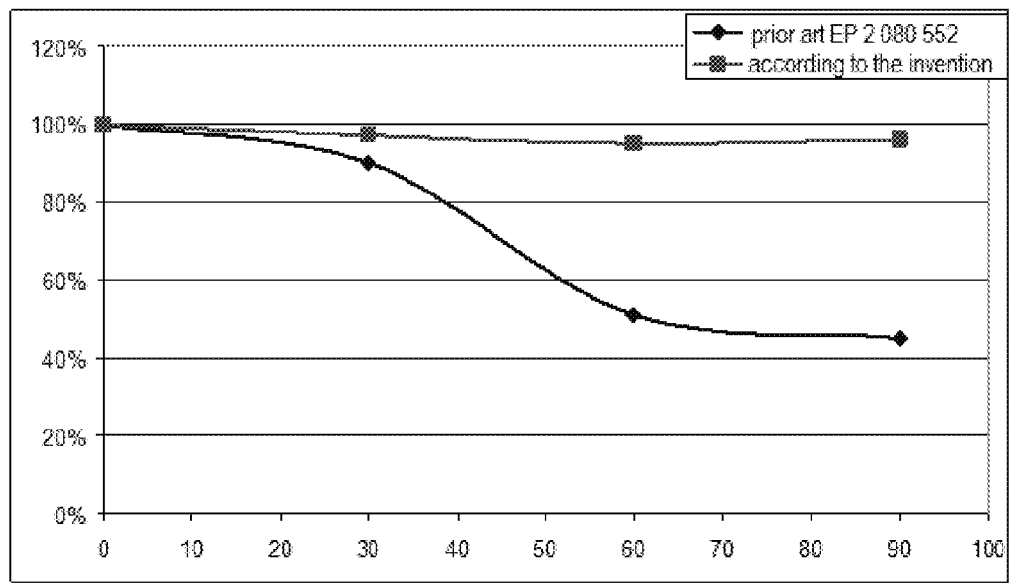

PROCESS FOR MANUFACTURING POLYSILOXANE MICROCAPSULES THAT ARE FUNCTIONALIZED AND ARE NOT VERY POROUS

The present invention relates to a method for encapsulating products that can have lipophilic or hydrophilic properties in a polysiloxane membrane that is particularly impervious, as well as a method for evaluating the imperviousness of said capsules.

Microcapsules are used in many fields for containing and providing metered or even programmed delivery of products, for example active ingredients or even medicinal products, in many cases. Commonly, it is for example a matter of including an active ingredient in a cosmetic. Increasingly, applications are being proposed for including microcapsules of active ingredients in any type of object, for example in textile objects, which are then sometimes called "texticaments", for delivering these active ingredients during the life and use of said objects.

Most of the time, the membrane of the microcapsules consists of organic materials such as polymers or oils. However, most polymer membranes have poor chemical properties, low mechanical strength and thermal stability. There are, however, some interesting alternatives such as melamine formol resins, but the increasingly strict legislation relating to them will ultimately prevent their use.

The use of a membrane based on polysiloxane makes it possible to overcome some of these drawbacks, as proposed for example by patent U.S. Pat. No. 6,855,335, which describes the manufacture of microcapsules by basic hydrolysis of TEOS in the presence of APS. However, these techniques have relatively long process times, for example of the order of 15 to 24 hours, and problems of reliability with respect to the structures obtained.

Patent EP 2,080,552 proposes a method for encapsulating a lipophilic product in a polysiloxane membrane based on tetraethoxysilane (TEOS) and methyltriethoxysilane (MTES). This method has considerable advantages in terms of harmlessness of the components, as well as good uniformity of the microcapsules and improved process times, of the order of 4 to 5 hours.

However, the microcapsules obtained are rather porous, which makes the encapsulation of volatile products, often lipophilic products, for example perfumes, difficult and unreliable.

Document FR 2,937,248 discloses a method for encapsulating an active principle in a polymer envelope formed from a compound of the silsesquioxane type, which uses one or more strong acids for hydrolysis, for example hydrofluoric acid. Now, such acids are very troublesome in many applications, for example for products that must be in contact with a user.

One purpose of the invention is to overcome the drawbacks of the prior art.

More particularly, one purpose of the invention is to improve the imperviousness of the capsules while maintaining good performance and the good qualities of uniformity of the structures obtained and of harmlessness, such as are obtained by the method described in patent EP 2,080,552.

Moreover, it may be useful to combine the microcapsules obtained with other compounds with which they are mixed or combined.

Another purpose of the invention is also to supply capsules comprising groups on the surface permitting functionalization of these capsules.

DISCLOSURE OF THE INVENTION

For this purpose, the invention proposes a method for encapsulating a lipophilic product in a polysiloxane membrane, for example oils, butters, perfumes. According to the invention, the encapsulation method comprises the following steps:

a) formation of droplets by an emulsion between an oily phase containing the product to be encapsulated and an acidic aqueous phase heated to around 50° C. and in the presence of surfactants;

b) addition and hydrolysis of at least one silane in order to obtain a silanol;

c) increasing the pH in order to start condensation of the silanol to form a first membrane around the droplets of the product to be encapsulated;

d) lowering the pH;

e) increasing the pH in order to obtain new or better condensation of the silanol or silanols around the droplets of the product to be encapsulated.

Capsules containing products having hydrophilic properties can also be obtained according to the invention.

According to a particular feature of the invention, step e) further comprises the addition of at least one silane, for example before increasing the pH, possibly a prehydrolysed silane.

Optionally, the silane added during step e) can moreover be, or comprise, a silane different from the silane or silanes added during step b), or even a silane that will not bind to it or to them. Thus, a second membrane forms around the droplets of the product to be encapsulated, during the new condensation of silanol during step e).

The invention thus makes it possible to obtain a double-layer membrane, or double membrane, further improving the imperviousness, in particular for containing volatile substances.

The method according to the invention represents a duration of the same order of magnitude as that previously described by document EP 2,080,552, or a little longer by about one hour, of the order of 5 to 6 hours. The production time is thus still far shorter than those provided by other techniques of the prior art, while maintaining good qualities of harmlessness and biocompatibility.

Nature of the Silane or Silanes

Preferably, at least one silane added in step b), or step e), or both, is a silane of the type:

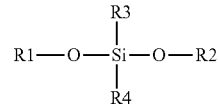

in which the four groups R1, R2, R3 and R4 can be different from one other or identical to one another, wholly or partly.

In this silane, these four groups R1, R2, R3 and R4 are selected from: alkyl, aryl, alkaryl, alkylamine, hydroxyl, ether, ester, acid, Cl, Br, I, F, or an ethoxy group possibly hydrolysed (for R4), or a group of the type:

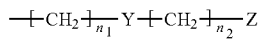

with:
n1=0 to 8 and n2=0 to 10; and
Y is selected from: O, NH, S, Si, NR'; and
Z is selected from: CH$_3$, NH$_2$, SH, Cl, Br, I, Cl, glycosidic group, hydroxyl, acid, ether, ester, amide, NH—R', NR'—R" and in which (for Y and Z):

R' is selected from alkyl, aryl, alkaryl, alkylamine, ether, ester, ketone, branched ring, and
R" is selected from: alkyl, aryl, alkaryl, alkylamine

EXAMPLES OF SILANES

By way of example, one or more of the silanes used in step b), or step e), or both, can be selected from the following substances:
(3-(trimethoxysilyl)propyl)diethylenetriamine,
(3-chloropropyl)triethoxysilane, 1-[3-(trimethoxysilyl)]-propylurea,
3-[2-(2-aminoethylamino)ethylamino]propyl-trimethoxysilane,
3-aminopropyldiethoxymethylsilane, 3-aminopropylmethyldiethoxysilane,
3-aminopropyltriethoxysilane, 3-aminopropyltrimethoxysilane,
3-glycidyloxypropyltriethoxysilane, 3-mercaptopropyltrimethoxysilane,
3-methacryloxypropyltrimethoxysilane, aminopropylmethyldiethoxysilane,
bis(3-triethoxysilylpropyl)amine, diethoxydimethylsilane,
methyltriethoxysilane (MTES), methyltrimethoxysilane,
N-(2-aminoethyl)-3-aminopropyltrimethoxysilane, phenyltriethoxysilane, propyltrimethoxysilane, tetraethoxysilane, tetraethylorthosilicate (TEOS), tetramethylorthosilicate, triethoxy(octyl)silane,
tris[3-(trimethoxysilyl)-propyl]isocyanurate, vinyltriethoxysilane, vinyltrimethoxysilane.

The following table presents several combinations of choices of silanes which were tested by the inventors:

| step b) | | step e) | |
|---|---|---|---|
| TEOS | tetraethoxy(octyl)silane | | |
| TEOS | MTES | | |
| TEOS | 3-aminopropyldiethoxymethylsilane | | |
| TEOS | MTES | 3-aminopropyl diethoxymethylsilane | |
| TEOS | phenyltriethoxysilane | | |
| TEOS | 1-[3-(trimethoxysylil)-propyl]urea | | |
| TEOS | triethoxyoctylsilane | | |
| TEOS | diethoxydimethylsilane | | |
| TEOS | 3-aminopropyltriethoxysilane | | |
| TEOS | tris(3-trimethoxysilylpropyl)isocyanate | | |
| TEOS | phenyltriethoxysilane | diethoxydimethylsilane | |
| TEOS | phenyltriethoxysilane | diethoxydimethylsilane | 3-aminopropyl triethoxysilane |
| TEOS | diethoxydimethylsilane | | 3-aminopropyl diethoxymethylsilane |
| TEOS | diethoxydimethylsilane | | |
| TEOS | 3-aminopropyldiethoxymethylsilane | | |
| TEOS | diethoxydimethylsilane | | tris(3-trimethoxysilyl-propyl) isocyanate |
| TEOS | diethoxydimethylsilane | | triethoxyoctylsilane |
| TEOS | diethoxydimethylsilane | | phenyltriethoxysilane |
| TEOS | diethoxydimethylsilane | | 1-[3-(trimethoxysilyl)-propyl]urea |
| TEOS | MTES | | 3-aminopropyl diethoxymethylsilane |
| TEOS | diethoxydimethylsilane | | 3-[2-(2-aminoethyl amino)ethylamino]propyl-trimethoxysilane |
| TEOS | diethoxydimethylsilane | (3-chloropropyl) triethoxysilane) | |
| TEOS | diethoxydimethylsilane | triethoxy(octyl)silane | |

Preferably, but not necessarily, step b) comprises adding at least two silanes, for example, on the one hand, TEOS and, on the other hand, at least one second, different silane.

Preferably, step c) is stopped while silanol groups still remain.

Moreover, according to an optional particular feature of the invention, at least one silane added in step e) is a functionalized silane comprising for example an amine or chlorinated function. The presence of functionalizing groups, for example NH$_2$, supplies precursors for the formation of covalent bonds that can bind to other compounds, selected in relation to additional characteristics of association or fixation that are required for the microcapsules produced, for example in order to obtain a bond to the hydroxyl functions present in the cellulose of cotton and thus obtain fixation of the capsules to the fabric.

Preparation of the Microcapsules

The invention proposes the preparation of microcapsules containing compounds that can have lipophilic or hydrophilic properties, the polysiloxane double membrane of which means they can be more impervious than in the prior art. This membrane is sufficiently impervious to be used for encapsulating volatile compounds. The developments of the invention also include the elaboration of a method allowing comparison of the imperviousness of the microcapsules between different preparation methods.

Microcapsules were manufactured according to the invention, containing a preparation based on an oily phase, a sunflower oil, containing a volatile compound, limonene, and a non-volatile compound, benzyl salicylate. The method according to the invention was developed starting from the encapsulation method described in patent EP 2,080,552, and the manufacturing protocol is only described here where it differs.

This encapsulation according to the invention uses an acidic aqueous phase, with a pH between 2.5 and 4.5, for example 3, obtained with one or more weak acids, and preferably a mixture of acetic acid and formic acid, and which is heated to between 40° C. and 70° C., and preferably to 50° C.

Surfactants, at least one of which is cationic, for example derivatives of cellulose such as for example a cationic derivative of hydroxyethylcellulose, are added to this aqueous phase. Then an oily phase is added, composed of sunflower oil, benzyl salicylate and limonene.

With vigorous stirring, an oil-in-water emulsion is formed comprising oil droplets containing the products to be encapsulated.

Then tetraethoxysilane (TEOS) and another silane, for example dimethyldiethoxysilane, phenyltriethoxysilane, or methyltriethoxysilane (MTES), are added. The presence of acid will hydrolyse the silanes, which will form silanols and migrate to the water/oil interface around the droplets, with for example the reactions:

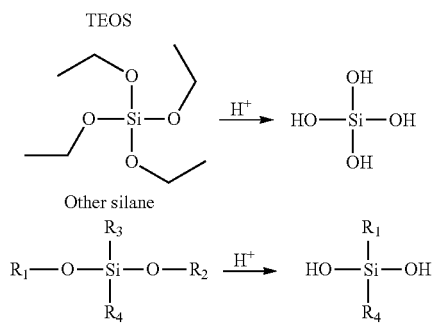

Then the pH is increased again using a base up to a value between 4.5 and 6 and preferably 5.5, for example ammonia or soda, or diethanolamine, or ethanolamine. This increase in pH will permit condensation to begin and thus form a first membrane around the droplets containing the product (or the products) to be encapsulated. The duration of this condensation is adjusted so that silanol groups (Si—OH) remain present on the surface of the membrane formed, to a value between 20 and 40 minutes, and preferably about 30 minutes.

This results in partial condensation and formation of a membrane, with, for example, the following reaction with a trihydroxylated silane:

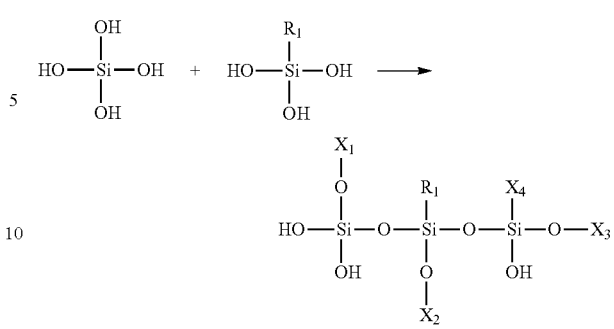

with:

$X_1$, $X_2$, $X_3$=silylated polymer chains or H; and $X_4$=silylated polymer chains, H or $R_1$.

The pH is then lowered again to between 2.5 and 4.5, and preferably around 3.80, for a duration of at least 5 minutes, and preferably about 10 minutes, for example, by means of one or more weak acids, and preferably a mixture of formic acid and acetic acid. This acidification stops the condensation and creates the conditions for a new hydrolysis.

In a first embodiment, a silane is then added. Optionally, it can be a prehydrolysed silane, which makes it possible to complete the operation of hydrolysis of the acidic medium. This also makes it possible to obtain $NH_3^+$ groups in addition to the hydroxyl groups in the case of functionalization by amine groups. In the case when a functionalized membrane is required, a functionalized silane is selected from those mentioned above, for example, an aminosilane or a chlorinated silane, functionalizing groups (for example $NH_2$) of which will promote the subsequent formation of covalent bonds.

For example, experiments have given good results when carried out with a non-functionalized silane for step b) (for the first membrane) and a functionalized silane for step e) (for the second membrane).

By way of example, prehydrolysis of the aminosilane comprises the reaction:

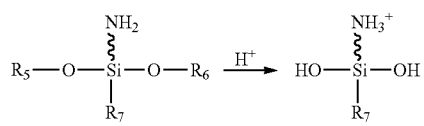

with R5, R6 and R7 described as above for R1, R2 and R3.
NOTE: R7, which can be an ether group, can also be hydrolysed.

In a second embodiment, which also gives good results for imperviousness, step e) of increasing the pH is carried out without adding silane or adding the same silane as in step b).

In both embodiments, the pH is then increased again to a value comprised between 4.5 and 7, and preferably about 5.5, by means of a base, for example ammonia or soda, or diethanolamine, or ethanolamine. Condensation is carried out between the silanol groups still present of the first membrane and those of the silane (or aminosilane) possibly added, with for example the following reaction:

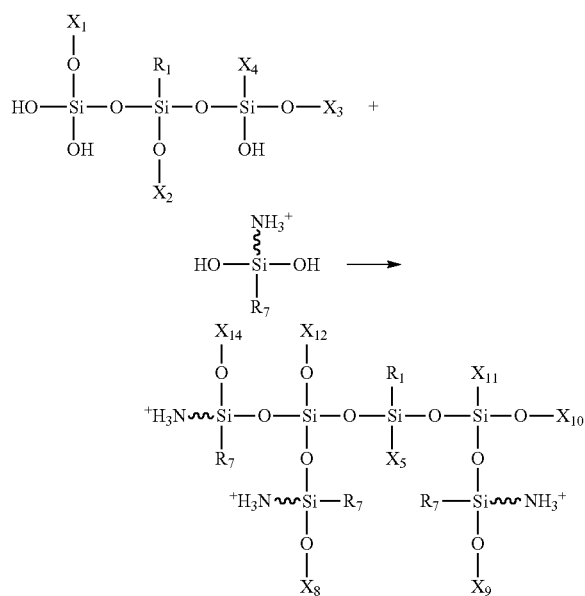

with:

$X_5$ to $X_{14}$=silylated polymer chain or H;

or $X_{11}$=silylated polymer chain, H or $R_1$.

If R7 is hydrolysed, the hydroxyl group obtained can then also give rise to a polymer chain during condensation, which gives additional possible choices of structure.

An impervious membrane is thus formed around the droplets containing the product or products to be encapsulated, which membrane is also functionalized in the case of an aminosilane.

Finally, a "slurry" is obtained, i.e. a suspension of microcapsules in an aqueous phase. This suspension can, for example, be converted according to known methods to provide a powder of microcapsules, a form for which the method according to the invention offers particularly good performance.

Imperviousness Tests

The microcapsules prepared as described above were then tested to verify their imperviousness, by the following method.

The microcapsules prepared contain, within their sunflower oil phase:
- a pure chemical compound that is lipophilic and volatile: (R)-limonene, and
- a pure chemical compound that is lipophilic and non-volatile: benzyl salicylate.

To evaluate the porosity of the microcapsules, samples of slurries are heated at different temperatures and for different durations, and analysis by GCMS based on the areas of the peaks of limonene and of benzyl salicylate is carried out to determine the amounts of these two substances present in the capsules.

At a time $T_0$, for a given batch of microcapsules, the ratio of the amounts of volatile and non-volatile compounds is measured, in order to obtain the ratio:

$$X = \frac{\text{Quantity of volatile substance}}{\text{Quantity of non-violatile substance}}$$

This batch of microcapsules is heated in a stove, to a temperature for example of 80° C. and/or 120° C. or between the two, or even to 160° C.

After heating in the stove, the ratio of the amounts of volatile and non-volatile compounds is measured again, in order to obtain the ratio:

$$Y = \frac{\text{Quantity of volatile substance}}{\text{Quantity of non-volatile substance}}$$

The ratio of ratios X and Y, i.e. before and after heating in the stove, gives a value indicating the porosity of the capsules.

A ratio Y/X=100% indicates that the capsules are indeed impervious. A value below 100% indicates that a proportion of the volatile compounds escaped, and therefore that the capsules are porous. The greater the porosity of the capsules, the lower the ratio Y/X.

The ratios Y/X are determined for different heating times T for different microcapsules.

By plotting Y/X=f(T) for each slurry, comparative porosity curves are obtained.

It is thus possible to evaluate the imperviousness of the capsules obtained according to different protocols.

Thus, FIG. 1 illustrates results of tests of comparative porosity, according to the heating time, between:
- on the one hand, capsules with a single membrane obtained according to the prior art as described in document EP 2,080,552, represented by the descending curve with diamonds, and
- on the other hand, capsules with a double membrane produced according to the invention with an aminosilane, represented by the stable curve with squares.

This curve is plotted from the following results:

| duration | single membrane according to the prior art | double membrane according to the invention |
|---|---|---|
| 0 min | 100% | 100% |
| 30 min | 90% | 97% |
| 60 min | 51% | 95% |
| 90 min | 45% | 96% |

It can be seen that the double membrane according to the invention gives much better imperviousness, especially at 60 min and 90 min.

Similarly, the following table presents the results of the same comparative porosity tests performed for microcapsules with a single membrane according to the invention, as described above for the second embodiment:

| duration | single membrane according to the invention - test 1 | single membrane according to the invention - test 2 |
|---|---|---|
| 0 min | 100% | 100% |
| 30 min | 88% | 92% |
| 60 min | 79% | 99% |
| 90 min | 84% | 96% |

Relative to the microcapsules with a single membrane according to the prior art (results in the preceding table), it can be seen that the method according to the invention gives a non-negligible improvement even in the embodiment with a single membrane.

It can thus be seen that the method according to the invention makes it possible to obtain a true imperviousness, even for durations where the capsules according to the prior art lose 55% of the volatile compounds that they contain. This represents a very important advantage, for example for improving the shelf life or expiry date of many products, for example "texticaments" or textiles with a cosmetic component, and in varied environmental situations.

This technique has thus made it possible to validate the improvements of imperviousness provided by the encapsulation method according to the invention.

Of course, the invention is not limited to the examples that have just been described, and numerous adjustments can be made to these examples without exceeding the scope of the invention.

The invention claimed is:

1. A method for encapsulating one or more products that can have lipophilic or hydrophilic properties in a polysiloxane double membrane, the method consisting of the following steps:
   a) forming droplets by an emulsion between an oily phase containing the product to be encapsulated and an acidic aqueous phase heated between 40° C. and 70° C., at pH between 2.5 and 4.5, and in the presence of surfactants;
   b) adding and hydrolyzing at least one silane in order to obtain a silanol;
   c) increasing the pH from 2 to 3 up to a value in the range from 4.5 to 6 by adding at least one base in order to start condensation of the silanol to form a first membrane around the droplets of the product to be encapsulated;
   d) lowering the pH to a value in the range from 2.5 to 4.5 by adding one or more weak acids to stop the condensation;
   e) adding and hydrolyzing at least one other silane which can be different from or the same as the silane or silanes added during step b);
   f) increasing the pH up to a value in the range from 4.5 to 7 by adding at least one base in order to obtain new or better condensation of the silanol to form a second membrane around the droplets of the product to be encapsulated, the condensation being carried out between the silanol groups still present of the first membrane and those of the silane of step e), resulting in the formation of
   a second membrane around the droplets of the product to be encapsulated.

2. The method according to claim 1, characterized in that at least one silane added in step b), or step e), or both, is a silane of the type:

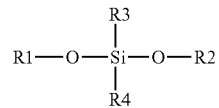

in which the four groups R1, R2, R3 and R4 can be different from one other or identical to one another, wholly or partly;
and in which said groups R1, R2, R3 and R4 are selected from: alkyl, aryl, alkaryl, alkylamine, hydroxyl, ether, ester, acid, Cl, Br, I, F, or an ethoxy group possibly hydrolysed for R4, or a group of the type:

with:
$n_1 = 0$ to 8 and $n_2 = 0$ to 10; and
Y is selected from: O, NH, S, Si, NR'; and
Z is selected from: $CH_3$, $NH_2$, SH, Cl, Br, I, Cl, glycosidic group, hydroxyl, acid, ether, ester, amide, NH—R', NR'—R"
and in which:
R' is selected from alkyl, aryl, alkaryl, alkylamine, ether, ester, ketone, branched ring, and
R" is selected from: alkyl, aryl, alkaryl, alkylamine.

3. The method according to claim 1, characterized in that one or more silanes used in step b), or step e), or both, is selected from the following substances:
(3-(trimethoxysilyl)propyl)diethylenetriamine,
(3-chloropropyl)triethoxysilane, 1-[3-(trimethoxysilyl)]-propylurea,
3-[2-(2-aminoethylamino)ethylamino]propyltrimethoxysilane,
3-aminopropyldiethoxymethylsilane, 3-aminopropylmethyldiethoxysilane,
3-aminopropyltriethoxysilane, 3-aminopropyltrimethoxysilane,
3-glycidyloxypropyltriethoxysilane, 3-mercaptopropyltrimethoxysilane,
3-methacryloxypropyltrimethoxysilane, aminopropylmethyldiethoxysilane,
bis(3-triethoxysilylpropyl)amine, diethoxydimethylsilane, methyltriethoxysilane (MTES),
methyltrimethoxysilane, N-(2-aminoethyl)-3-aminopropyltrimethoxysilane, phenyltriethoxysilane, propyltrimethoxysilane, tetraethoxysilane, tetraethylorthosilicate (TEOS), tetramethylorthosilicate, triethoxy(octyl)silane,
tris[3-(trimethoxysilyl)-propyl]isocyanurate, vinyltriethoxysilane, vinyltrimethoxysilane.

4. The method according to claim 1, characterized in that step b) comprises the addition of TEOS and of at least one second silane.

5. The method according to claim 1, characterized in that in step e) at least one silane added is a functionalized silane comprising an amine or chlorinated function.

6. The method according to claim 5, characterized in that the silane added in step e) is prehydrolysed.

7. The method according to claim 1, characterized in that step a) comprises the following substeps:
   a) heating an acidic aqueous phase between 40° C. and 70° C.;
   b) addition of surfactant;
   c) addition of an oily phase comprising the product to be encapsulated; and
   d) stirring in order to form an oil-in-water emulsion.

8. The method according to claim 1, characterized in that step c) is stopped while silanol groups still remain.

9. The method according to claim 1, characterized in that in step a) or in step d) or both, acidification is obtained by means of acetic acid or formic acid or both.

10. The method according to claim 1, characterized in that in step c) or step f) the base is selected from ammonia, soda, diethanolamine, or ethanolamine.

11. The method according to claim 1, characterized in that the surfactants comprise a cellulose derivative.

12. The method according to claim 7, wherein step a) comprises the following substeps:
   a1) heating an acidic aqueous phase at 50° C.;
   a2) addition of surfactant;
   a3) addition of an oily phase comprising the product to be encapsulated;
   a4) stirring in order to form an oil-in-water emulsion.

13. The method according to claim 1, wherein the aqueous phase in step a) has a pH of 3.

14. The method according to claim 1, wherein the pH in step c) is increased from 2 to 5.5.

15. The method according to claim 1, wherein the pH in step d) is lowered to 3.8.

16. The method according to claim 1, wherein the pH in step f) is increased to 5.5.

* * * * *